United States Patent
Ooishi et al.

(10) Patent No.: US 8,647,280 B2
(45) Date of Patent: Feb. 11, 2014

(54) ULTRASONIC PROBE AND METHOD FOR MANUFACTURING ULTRASONIC PROBE

(75) Inventors: Michiko Ooishi, Kawasaki (JP); Satoru Asagiri, Yokohama (JP); Takashi Togasaki, Yokohama (JP); Takeshi Miyagi, Fujisawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 13/424,873

(22) Filed: Mar. 20, 2012

(65) Prior Publication Data

US 2012/0245470 A1    Sep. 27, 2012

(30) Foreign Application Priority Data

Mar. 24, 2011 (JP) ................................. 2011-066748

(51) Int. Cl.
*A61B 8/14* (2006.01)
(52) U.S. Cl.
USPC ......................................... 600/459; 600/437
(58) Field of Classification Search
USPC ................................................. 600/437–469
See application file for complete search history.

(56) References Cited

U.S. PATENT DOCUMENTS

| 6,894,425 | B1 | 5/2005 | Solomon et al. |
| 7,654,961 | B2 | 2/2010 | Tezuka |
| 2011/0198151 | A1* | 8/2011 | Oakley et al. ................ 181/290 |
| 2011/0237952 | A1 | 9/2011 | Ooishi et al. |
| 2011/0316387 | A1 | 12/2011 | Togasaki et al. |
| 2012/0123268 | A1* | 5/2012 | Tanaka et al. ................ 600/443 |

FOREIGN PATENT DOCUMENTS

JP    5-103397    4/1993

* cited by examiner

*Primary Examiner* — Sanjay Cattungal
(74) *Attorney, Agent, or Firm* — Oblon, Spivak, McClelland, Maier & Neustadt, L.L.P.

(57) ABSTRACT

An ultrasonic probe includes, a transducer, a substrate includes electrodes formed on a front surface and a back surface and electronic components, first flexible wire substrates connected in such a manner that a first end is connected to the transducer and a second end is connected to a electrode at a side of the front surface of the substrate, second flexible wire substrates connected in such a manner that a first end is connected to the transducer and a second end is connected to a electrode at a side of the back surface of the substrate, and a dummy materials including the same rigidity and thickness as those of the first flexible wire substrate is arranged at a space, adjacent to a electrode at the side of the front surface of the substrate, corresponding to the second end of the second flexible wire substrate.

7 Claims, 8 Drawing Sheets

ULTRASONIC PROBE AND METHOD FOR MANUFACTURING ULTRASONIC PROBE

CROSS-REFERENCE TO RELATED APPLICATIONS

This application is based upon and claims the benefit of priority from prior Japanese Patent Application No. 2011-066748, filed Mar. 24, 2011, the entire contents of which are incorporated herein by reference.

FIELD

An embodiment relates to an ultrasonic probe and manufacturing method of the same, wherein the ultrasonic probe transmits ultrasonic waves using a transducer in which piezoelectric elements are arranged in, e.g., a two-dimensional (2-D) array form, and receives a reflected ultrasonic waves.

BACKGROUND

In recent years, ultrasonic waves diagnostic apparatus for medical echo imaging analysis uses a 2-D array ultrasonic probe capable of diagnosing of a three-dimensional motion picture in real-time. In the 2-D array ultrasonic probe, ultrasonic waves are transmitted from a transducer arranged in a 2-D array form, and the reflected ultrasonic waves are received by the transducer. Detected signals are sent to a main body of an inspection apparatus and through a cable, so that the signals are subjected to image processing and used for diagnosis and the like.

Figure 3A:
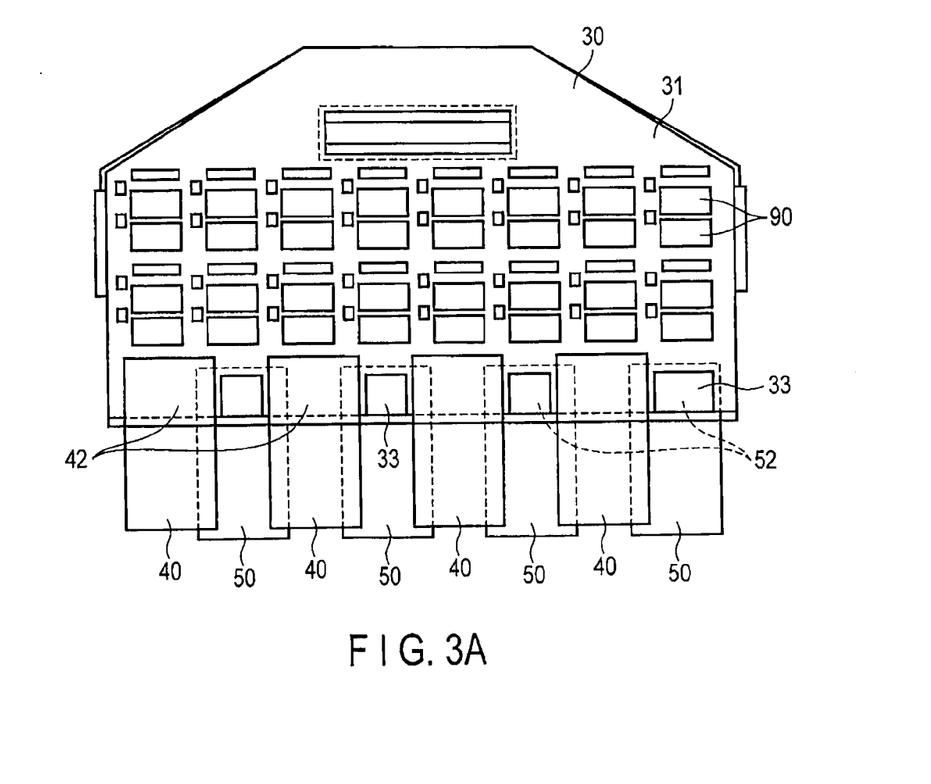
FIG. 3A is a plan view illustrating a substrate incorporated into the ultrasonic probe.

In a convex-type 2-D array ultrasonic probe, there are transducers for several thousands piezoelectric elements are arranged in a 2-D convex array form, and a flexible wire substrate (FPC) is used to connect the transducer and the circuit board substrate (PCB). In FPC, electrodes are arranged alternately on a front surface and a back surface in the plan view of a PCB, so that wires are drawn from the transducer with the shortest distance from both surfaces of PCB and at the highest density (FIG. 3A).

When the electrodes of FPC is connected to a electrodes of PCB, an anisotropic conductive film (ACF) is used. At this occasion, the ACF is provided on the electrode pad on the front surface of the PCB, and the FPC is arranged thereon. In addition, for example, a polytetra fluoroethylene (PTFE) film (sheet material with a high degree of heat resistance and releasing property) is provided thereon, and the resin sheet is attached thereon by thermocompressive bonding using a heat tool. In this configuration, it is connected with the electrodes of the FPC and the electrodes of the PCB with the particles contained in ACF electrically. Likewise, an electrodes of FPC is also connected to electrodes provided on the back surface of the PCB.

The above ultrasonic probe involves the following problems. That is, there is a certain space between an FPC connected to a front surface PCB side and an FPC adjacent thereto. When the FPC at the back surface side is arranged at a position corresponding to this space, the rigidity of the PCB is insufficient for attachment by thermocompressive bonding using a heat tool. As a result, the FPC cannot follow deformation of the PCB, which reduces the flatness of the thermocompressive bonding surface. Therefore, the pressurizing force is insufficient, and this may cause defective of electric connection.

Accordingly, it is an object to provide an ultrasonic probe and a method for manufacturing the ultrasonic probe capable of solving the shortage of the pressurizing force and ensuring the connection by sufficiently ensuring the flatness of the thermocompressive bonding surface.

DETAILED DESCRIPTION

An ultrasonic probe according to one aspect includes a transducer, a substrate having electrodes formed on a front surface and a back surface and electronic components processing signal information obtained from the transducer, a plurality of first FPCs connected in such a manner that a first end is connected to the transducer and a second end is connected to a electrode at a side of the front surface of the substrate with a connection member interposed therebetween, and a plurality of second FPCs connected in such a manner that a first end is connected to the transducer and a second end is connected to a electrode at a side of the back surface of the substrate with a connection member interposed therebetween, wherein a dummy materials having substantially the same rigidity and thickness as those of the first FPC is arranged at a part, adjacent to a electrode at the side of the front surface of the substrate, corresponding to the second end of the second FPC.

Figure 1:
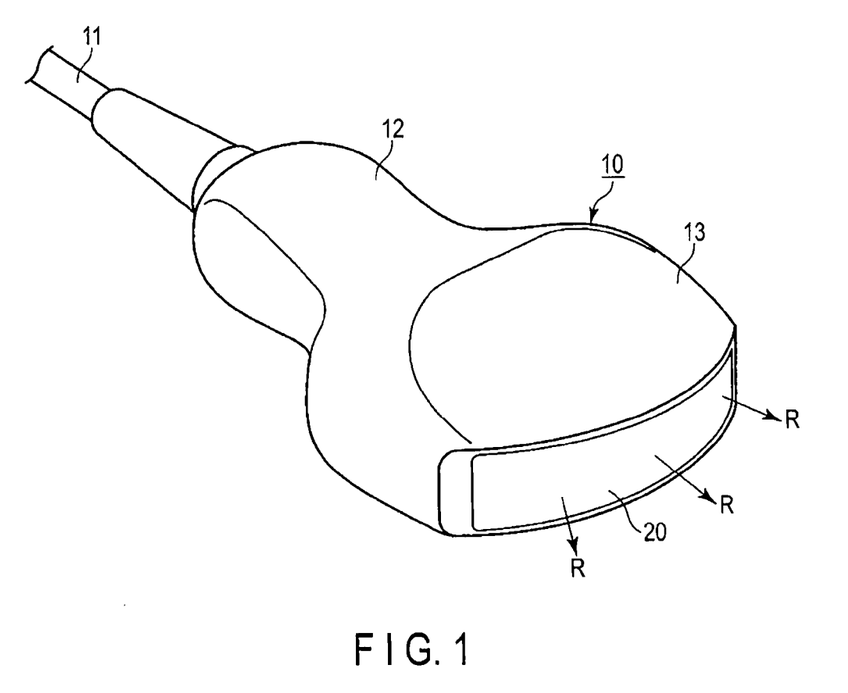
FIG. 1 is a perspective view illustrating an ultrasonic probe according to the present embodiment.
Figure 2:
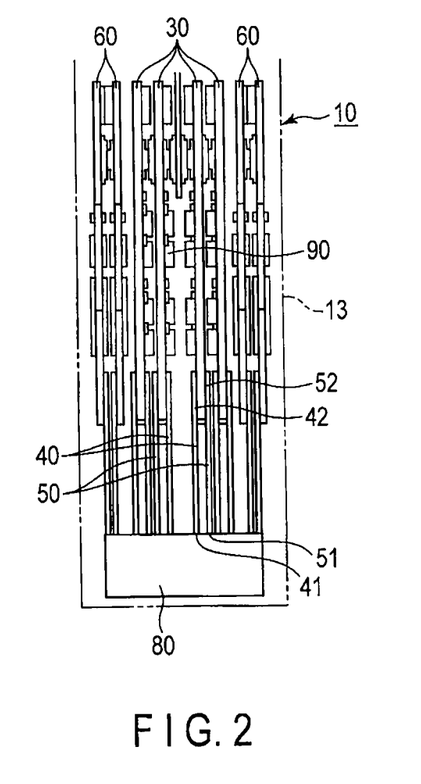
FIG. 2 is a cross-sectional view illustrating an essential part of the ultrasonic probe.
Figure 3B:
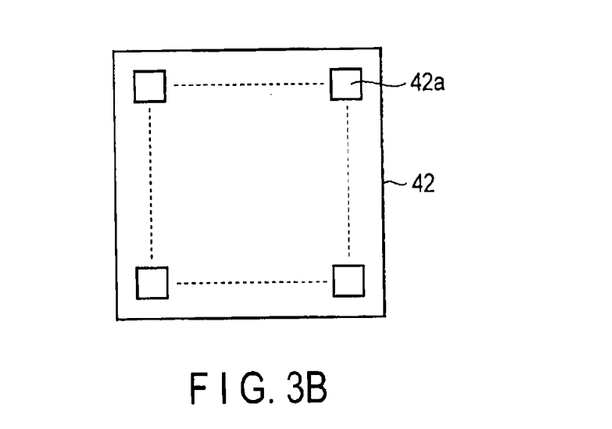
FIG. 3B is a plan view illustrating the second end of a first FPC connected to the substrate.
Figure 3C:
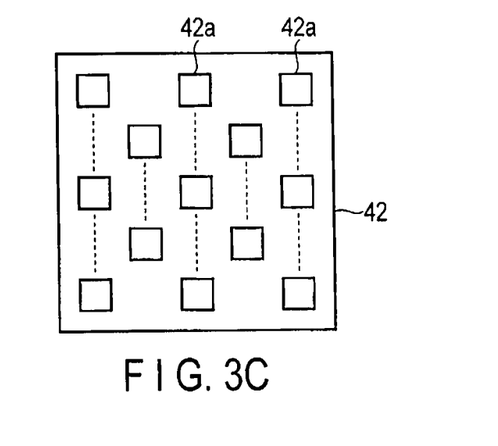
FIG. 3C is a plan view illustrating a modification of the second end.
Figure 3D:
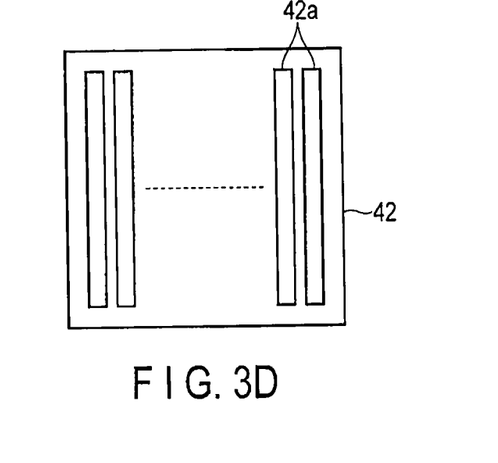
FIG. 3D is a plan view illustrating a modification of the second end.
Figure 4A:
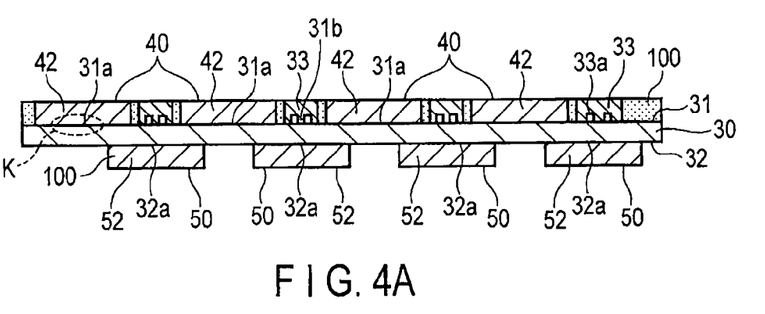
FIG. 4A is a cross-sectional view schematically illustrating a connection part between FPCs and the substrate of the ultrasonic probe.
Figure 4B:
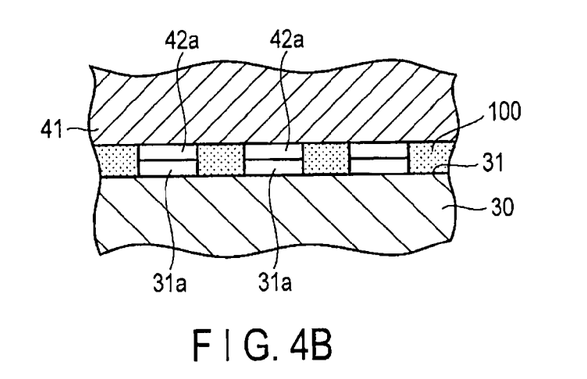
FIG. 4B is a cross-sectional view enlarging and illustrating K part indicated by a chain double-dashed line in FIG. 4A.

FIG. 1 is a perspective view illustrating an ultrasonic probe 10 according to the first embodiment. FIG. 2 is a cross-sectional view illustrating an essential part of the ultrasonic probe 10. FIG. 3A is a plan view illustrating a substrate 30 incorporated into the ultrasonic probe 10. FIGS. 3B, 3C, 3D are plan views illustrating the second end 42 of a first FPC 40 connected to the substrate 30. FIG. 4A is a cross-sectional view schematically illustrating a connection part between FPCs 40 and the substrate 30 of the ultrasonic probe 10. FIG. 4B is a cross-sectional view enlarging and illustrating K part indicated by a chain double-dashed line in FIG. 4A. In the figures, R denotes an ultrasonic wave irradiation direction.

The ultrasonic probe 10 is a convex-type 2-D array ultrasonic probe attached to an ultrasonic wave diagnosis apparatus through cable 11. The ultrasonic probe 10 includes a handle part 12 held by an operator and a head 13 in which a detection unit 20 is accommodated. In the head 13, a convex surface is formed in the ultrasonic wave irradiation direction (arrow R in FIG. 1).

As shown in FIG. 2, the detection unit 20 includes, at least a PCB 30 for processing a transmission/reception signals, first FPCs 40 respectively connected to electrodes 31a at the side of a front surface 31 of the convex side of this PCB 30, second FPCs 50 respectively connected to electrodes 32a at the side of a back surface 32, four PCBs 60 provided at the outer side of the PCB 30, third FPCs 70 respectively connected to these PCBs 60, and a transducer 80 arranged in a convex (convex-type) 2-D array form and connected to the first FPCs 40, the second FPCs 50, and the third FPCs 70.

In the first FPC 40, a first end 41 is connected to the transducer 80, and a second end 42 is connected to the PCB 30. In the second FPC 50, a first end 51 is connected to the transducer 80, and a second end 52 is connected to the PCB 30. It should be noted that are formed in the second end 42 electrode pads 42a.

Electronic components 90 such as a switch IC are mounted on the PCB 30 and the PCB 60, which are connected to the first FPC 40, the second FPC 50, the third FPC 70, and the cable 11.

As shown in FIG. 3A, the first FPC 40 and the second FPC 50 are alternately arranged on the PCB 30 in a plan view. This is to connect them to the transducer 80 with the shortest distance at the highest density. As shown in FIG. 3B, the electrodes 42a connected to the electrode 31a are formed at the second end 42. As shown in FIGS. 3C and 3D, the electrodes 42a may be arranged as necessary according to the electrodes 31a.

The electrodes 31a on the front surface 31 of the PCB 30 and the first FPCs 40 are connected as shown in FIGS. 4A and 4B. FIG. 4B is a cross-sectional view enlarging and illustrating K portion indicated by a chain double-dashed line in FIG. 4A. That is, a dummy materials 33 having the same rigidity as the first FPC 40 is arranged at a space 31b, adjacent to the electrode 31a, corresponding to a second end 52 of the second FPC 50. An ACF (jointing material) 100 is used for connection between the electrode 31a and the second end 42 of the first FPC 40 and between the electrode 32a and the second end 52 of the second FPC 50.

The dummy materials 33 is made of the base material of the first FPC 40, i.e., a resin film. The dummy materials 33 has substantially the same rigidity and substantially the same thickness as the first FPC 40. When a metallic dummy electrode 33a is formed on the dummy materials 33, the rigidity similar to that of the first FPC 40 can be achieved. For a similar reason, a dummy electrode and the like may be provided on the front surface 31b of the substrate 30.

The ultrasonic probe 10 thus configured is manufactured as follows. That is, an electrode provided at the first end 41 of the first FPC 40 is connected to an electrode of the transducer 80.

Figure 5:
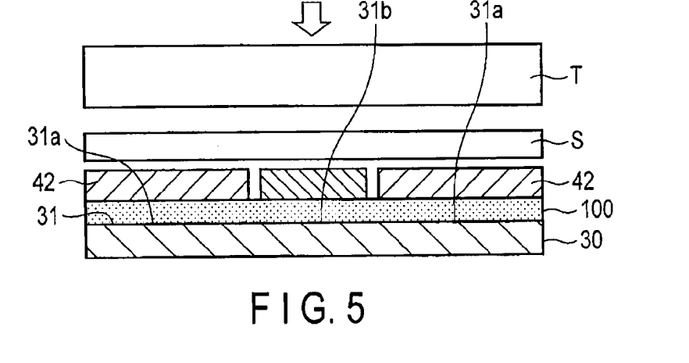
FIG. 5 is a cross-sectional view illustrating an essential part of manufacturing steps of the ultrasonic probe.
Figure 6:
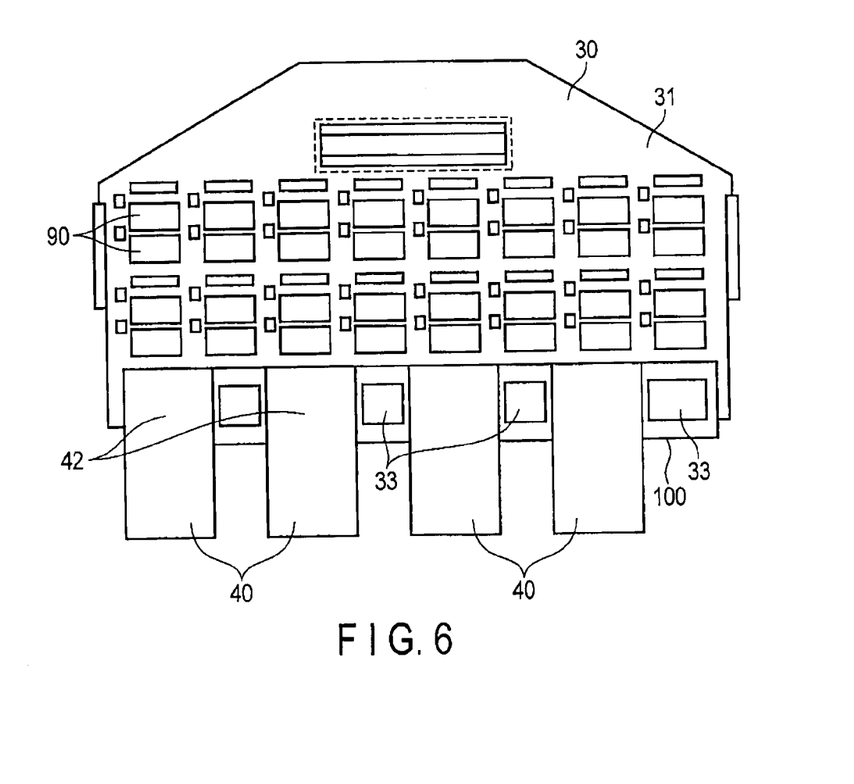
FIG. 6 is a plan view illustrating a manufacturing step of the ultrasonic probe.

Subsequently, as shown in FIGS. 5 and 6, the ACF 100 is attached to the electrode 31a and the space 31b adjacent to the electrode 31a. Subsequently, the electrode pads 42a at the second end 42 of the first FPC 40 is mounted on the electrode 31a formed on the front surface 31 of the PCB 30. The dummy materials 33 having the same rigidity as the first FPC 40 is arranged in the space 31b adjacent to the electrode 31a of the PCB 30.

As shown in FIG. 5, the second end 42 of the first FPC 40, the dummy materials 33, and the ACF 100 are attached to the PCB 30 by thermocompressive bonding using a crimping tool T with a resin sheet S interposed therebetween.

Figure 7:
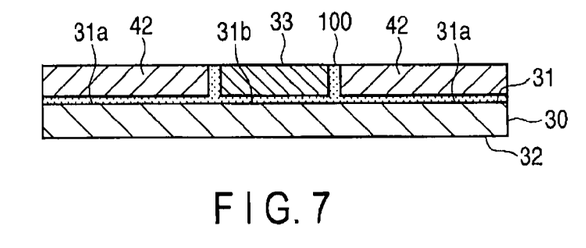
FIG. 7 is a cross-sectional view illustrating an essential part of manufacturing steps of the ultrasonic probe.

As shown in FIG. 7, the ACF 100 is temporarily melted by heat, and the ACF 100 fills gaps between the second end 42 of the first FPC 40, the dummy materials 33, and the electrodes 31a, and the spaces 31b. Thereafter, the ACF 100 hardens, and the surface becomes substantially flat.

Figure 8:
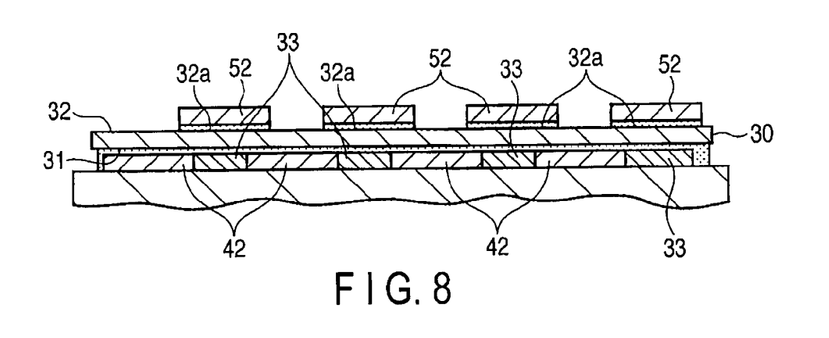
FIG. 8 is a cross-sectional view illustrating an essential part of manufacturing steps of the ultrasonic probe.

Subsequently, the PCB 30 is flipped over, and as shown in FIG. 8, the ACF 100 is attached to the bonding surface including the electrodes 32a formed on the back surface 32 of the PCB 30. Subsequently, the electrode at the second end 52 of the second FPC 50 is provided on the electrode 32a formed on the back surface 32 of the PCB 30, and is attached by thermocompressive bonding using the crimping tool T.

At this occasion, the dummy materials 33 is arranged, on the front surface 31 of the PCB 30, at the position corresponding to the second end 52 of the second FPC 50. Therefore, sufficient flatness is ensured. Therefore, the second end 52 of the second FPC 50 does not move when pressurized with the crimping tool T. This allows sufficient pressing force to be applied, which ensures connection between the second end 52 of the second FPC 50 and the electrode 32a.

In the ultrasonic probe 10 thus configured, the dummy materials 33 having the rigidity and the thickness equivalent to those of the first FPC 40 is arranged at the position corresponding to the second FPC 50 at the side opposite to the PCB 30, so that when the second FPC 50 is attached by thermocompressive bonding, the second FPC 50 does not move to the side of the substrate even when the second FPC 50 is pressed by the crimping tool T. Therefore, the second FPC 50 can be reliably attached by thermocompressive bonding.

In other words, whichever position the second FPC 50 is arranged, uniform pressure can be applied, which allows reliable connection of the second FPC 50. Therefore, the second FPC 50 can be arranged more flexibly. For example, when the distance to the transducer 80 is reduced and the wirings are made at high density, the number of channels of the transducer 80 can be increased, which increase the resolution of images.

Residual materials produced by cutting out the first FPCs 40, the second FPCs 50, and the third FPCs 70 from the base resin may be used for the dummy materials 33.

Figure 9A:
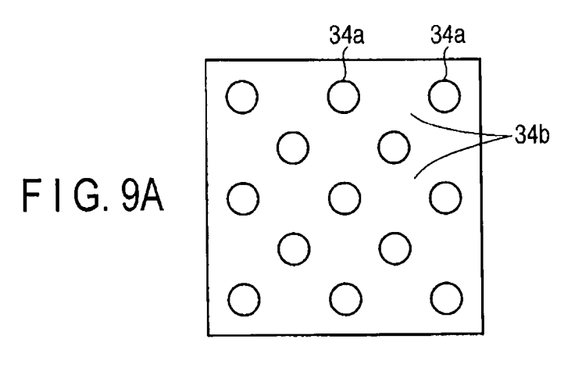
FIG. 9A is a plan view illustrating a modification of a dummy materials incorporated into the ultrasonic probe.

FIG. 9A is a figure illustrating a modification where dummy materials 34 are used instead of the dummy materials 33. The dummy materials 34 has paths 34b in a direction parallel to the dummy electrodes 34a and the front surface 31 of the PCB 30. When the paths 34a are provided, the ACF 100 softened during the thermocompressive bonding is more likely to flow, and this allows the gaps between the first FPCs 40 and the dummy materials 34 to be filled uniformly, which increases the degree of flatness. Therefore, the second FPC 50 can be connected more reliably.

Figure 9B:
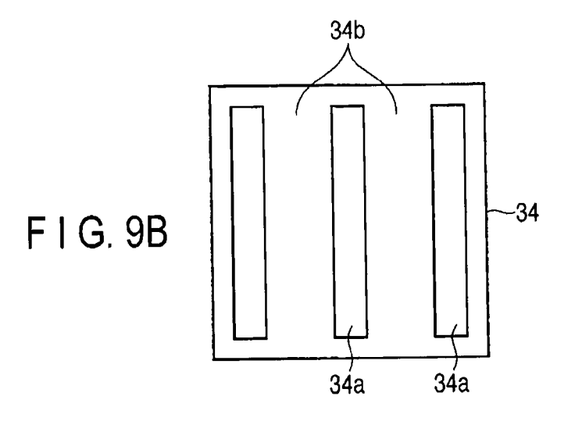
FIG. 9B is a plan view illustrating a modification of a dummy materials incorporated into the ultrasonic probe.
Figure 9C:
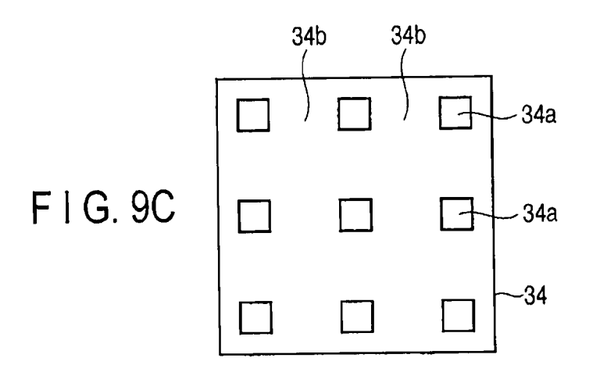
FIG. 9C is a plan view illustrating a modification of a dummy materials incorporated into the ultrasonic probe.

Likewise, FIGS. 9B and 9C are also plan views illustrating a dummy materials 34 according to a modification.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic probe comprising:
a transducer;
a first substrate comprising electrodes formed on a front surface and a back surface and electronic components processing signal information obtained from the transducer;
a plurality of first flexible wire substrates connected in such a manner that a first end is connected to the transducer and a second end is connected to an electrode at a side of the front surface of the first substrate with a connection member interposed therebetween;
a plurality of second flexible wire substrates connected in such a manner that a first end is connected to the transducer and a second end is connected to an electrode at a side of the back surface of the substrate with a connection member interposed therebetween; and
dummy materials including substantially the same rigidity and thickness as those of the first flexible wire substrate is arranged at a space, adjacent to an electrode at the side of the front surface of the first substrate, corresponding to the second end of the second flexible wire substrate.

2. The ultrasonic probe according to claim 1, wherein the connection material is an anisotropic conductive film.

3. The ultrasonic probe according to claim 1, wherein the dummy materials is the same material as a base material of the flexible wire substrate.

4. The ultrasonic probe according to claim 1, wherein the dummy materials has a path in parallel to the surface of the first substrate.

5. The ultrasonic probe according to claim 1, wherein the first flexible wire substrate and the second flexible wire substrate are alternately arranged on the it substrate in a plane view of the first substrate as seen in a thickness direction.

6. A method for manufacturing an ultrasonic probe in which a first flexible wire substrate and a second flexible wire substrate are connected to electrodes respectively formed on a front surface and a back surface of a first substrate on which electronic components processing signal information obtained from a transducer are mounted, the ultrasonic probe is manufactured by:
connecting a first end of the first flexible wire substrate to the transducer;
connecting a first end of the second flexible wire substrate to the transducer;
overlaying and arranging a jointing material on an electrode formed on the front surface of the first substrate and a space adjacent to the electrode;
arranging a second end of the first flexible wire substrate on the electrode formed on the front surface of the first substrate;
arranging dummy materials comprising substantially the same rigidity as the first flexible wire substrate on a space adjacent to the electrode formed on the front surface of the first substrate;
attaching the first flexible wire substrate, the dummy materials, and the jointing material toward a side of the first substrate by thermocompressive bonding;
overlaying and arranging a jointing material on an electrode formed on a back surface of the first substrate;
arranging a second end of the second flexible wire substrate on the electrode formed on the back surface of the first substrate; and
attaching the second flexible wire substrate and the jointing material toward a side of the first substrate by thermocompressive bonding.

7. A method for manufacturing an ultrasonic probe, using:
electronic components processing signal information obtained from a transducer;
a first substrate on which the electronic components are mounted, an electrode being provided on each of a front surface and a back surface of the first substrate;
a first flexible wire substrate having an end connected to the transducer and the other end positioned on the electrode on the front surface of the first substrate through a jointing material overlaid on the electrode and a component adjacent to the electrode; and
a second flexible wire substrate having an end jointed to the transducer,
the method comprising:
arranging dummy materials comprising substantially the same rigidity as the first flexible wire substrate on a space adjacent to the electrode formed on the front surface of the first substrate;
attaching the first flexible wire substrate, the dummy materials, and the jointing material toward a side of the first substrate by thermocompressive bonding;
overlaying and arranging a jointing material on an electrode formed on a back surface of the first substrate;
arranging a second end of the second flexible wire substrate on the electrode formed on the back surface of the first substrate; and
attaching the second flexible wire substrate and the jointing material toward a side of the first substrate by thermocompressive bonding.

* * * * *